United States Patent [19]

Fillers et al.

[11] Patent Number: 5,502,249
[45] Date of Patent: Mar. 26, 1996

[54] PROCESS FOR THE REMOVAL OF IODINE FROM ACETYL COMPOUNDS

[75] Inventors: Carl F. Fillers, Greeneville; Jerry A. Barron, Gray; Eric D. Middlemas, Johnson City, all of Tenn.

[73] Assignee: Eastman Chemical Company, Kingsport, Tenn.

[21] Appl. No.: 251,228

[22] Filed: May 31, 1994

[51] Int. Cl.⁶ .......................... C07C 51/42; C07C 51/573
[52] U.S. Cl. .......................... 562/608; 562/898; 203/28; 203/29; 203/86; 203/DIG. 6
[58] Field of Search ........................... 562/604, 608, 562/898; 203/28, 29, 86, DIG. 6

[56] References Cited

U.S. PATENT DOCUMENTS

| | | | |
|---|---|---|---|
| 4,029,553 | 6/1977 | Price | 562/519 |
| 4,036,940 | 7/1977 | McLane et al. | 423/503 |
| 4,664,753 | 5/1987 | Erpenbach et al. | 562/608 |
| 4,813,988 | 3/1989 | Bennett et al. | 62/18 |
| 5,300,685 | 4/1994 | Scates et al. | 562/608 |

*Primary Examiner*—Jose G. Dees
*Assistant Examiner*—Rosalynd A. Williams
*Attorney, Agent, or Firm*—J. Frederick Thomsen; John F. Stevens

[57] ABSTRACT

Disclosed is a process for the removal of iodine, including $I_2$, $I^-$ and iodine-containing organic compounds, from acetic acid or anhydride wherein an acetyl product stream comprising (i) acetic acid or acetic anhydride and (ii) iodine, one or more iodine-containing compounds or a mixture thereof is subjected to distillation in the presence of a packing material comprising iron, nickel, copper, or an alloy thereof.

8 Claims, No Drawings

PROCESS FOR THE REMOVAL OF IODINE FROM ACETYL COMPOUNDS

This invention pertains to the removal of iodine, including $I_2$, $I^-$ and iodine-containing organic compounds, from acetyl compounds such as acetic acid and acetic anhydride. More specifically, this invention pertains to a process for the reduction of the iodine content of acetyl streams contaminated with iodine and/or one or more iodine compounds by subjecting the iodine-contaminated acetyl stream to distillation in the presence of certain metal materials.

Various processes for the preparation of carboxylic acids and anhydrides, including the coproduction of carboxylic acids and anhydrides or carboxylic anhydrides and alkylidene dicarboxylates, by the catalytic carbonylation of alcohols, ethers, esters and/or olefins have been described extensively in the literature and, in some cases, have been used on a commercial scale. Typically, these carbonylation processes are carried out in the presence of a Group VIII metal and an iodine-containing compound such as, but not limited to, hydrogen iodide, an alkyl iodide such as methyl iodide, a phosphonium iodide, an alkali metal iodide, or an iodide salt of a number of other catalyst or promoter components. See, for example, S. W. Polichnowski, J. Chem. Educ., 1986, 63, 206 and U.S. Pat. Nos. 3,769,329, 4,374,070, 4,661,631 and 4,994,608. The carboxyl product-containing reactor effluents from such carbonylation processes commonly are subjected to conventional separation procedures, such as fractional distillation, which allows the recovery and recycle of both the volatile and non-volatile iodine containing compounds. Indeed, the economic operation of such processes depends, in part, upon such an effective recycle. In spite of the efficiency of most separation methods, however, small amounts of iodine-containing compounds, e.g., up to about 250 parts per million by weight (ppm) [I], typically are contained in the product. For certain end uses, purchasers require that the iodine content of carboxyl compounds be extremely low, e.g., <20 parts per billion by weight (ppb).

U.S. Pat. No. 4,036,940 discloses the use of a single type of catalyst (copper oxide/chromium oxide on alumina) for the recovery and recycle of iodine from hydrocarbon streams. There is no specific application of the recovery process to streams containing carboxylic acids. The method requires either a catalyst activation step carried out at 400°–450° C. (during which process hydrogen or carbon monoxide is passed over the bed resulting in the catalyst turning a bright red color) or one of these reductants is passed over the bed concurrently with the vaporized hydrocarbon stream being treated. During operation, the iodine removal bed is maintained at a temperature of 300°–500° C. and is able to retain 85.9–93.7% of the iodine flowing through it.

The method described in U.S. Pat. No. 4,036,940 requires high temperatures for activation (400°–450° C.) and operation (300°–500° C.). Such high temperatures are (i) incompatible with maintaining a high surface area catalyst (the bright red color of the reduced catalyst reported in this patent is characteristic of a highly sintered material) and (ii) would require a process stream containing acetic acid to be heated well beyond the point at which it becomes a vapor and is thus economically unattractive. In spite of, or possibly because of, the high operating temperatures required in this method, the highest demonstrated efficiency for iodine removal is 93.7%. This efficiency level is inadequate for producing carboxyl product streams that meet appropriate fitness-for-use criteria.

U.S. Pat. No. 4,792,420 discloses the use of expensive Group VIII, noble metal-containing catalysts in conjunction with hydrogen to reduce the level of iodine-containing impurities in carboxylic acid anhydride streams to a very low level. This patent specifically excludes streams that consist primarily of acetic acid, i.e., expressly limiting components other than carboxylic acid anhydrides to 25 weight percent or less of the total, and indicates that anhydrous conditions are to be employed.

European Patent Application Publication 372,993 describes the improvement of acetic acid permanganate times by treatment with hydrogen and a hydrogenation catalyst containing platinum, palladium, rhodium, ruthenium, osmium, iridium, nickel, or cobalt. Copper-containing catalysts are not mentioned and iodine levels are not determined. There is no specific teaching that the method will reduce the iodine content to <20 ppb and, in fact, mentions that the described method is useful in conjunction with other iodine removal methods. This patent primarily teaches the reduction of aldehydes and unsaturated aldehydes to the saturated aldehyde and/or alcohol, thus reducing the level of oxidizable material. The only analytical method reported is permanganate time.

Canadian Patent 1,234,149 (equivalent to EP 143,179) describes the treatment of acetic acid or acetic anhydride at 50° to 200° C., preferably 80° to 140° C., with hydrogen in the presence of a Group VIII noble metal such as ruthenium, osmium, iridium or, preferably rhodium, palladium or platinum finely distributed on a silica or alumina support. This treatment is said to reduce the iodine content, present as alkyl or aryl iodides and hydrogen iodide or phosphonium iodide salts, to acceptable, e.g., <20 ppb, levels. The residence time is 0.2 to 6 hours and treatment is carried out at a pressure of 0.5 to 10 bars. The catalyst is preferably separated by filtration and is discarded when its capacity is exhausted. A comparative example reveals that iodine removal is not acceptable when hydrogen is omitted.

Canadian Patent 1,279,655 (equivalent to EP 217,182) discloses an improvement to the process disclosed in CA 1,234,149 which involves the addition of carbon monoxide to the gaseous feed to overcome a serious defect. Apparently, in the absence of added carbon monoxide, catalyst activity decreases relatively rapidly, and efficient iodine removal then requires that the operating temperature of the catalyst bed be increased. At these increased temperatures excessive by-product formation (acetaldehyde, acetic acid and ethylidene diacetate when the stream being treated contains acetic anhydride) occurs. It was found that if the gas fed to the treating bed contains carbon monoxide then the formation of these reduced byproducts could be minimized.

The use of a heterogeneous noble metal catalyst according to the known processes cited above presents at least two significant disadvantages. The first is the cost of the noble metal catalysts. This is of particular concern as the catalyst is discarded when exhausted. Furthermore, in the above-described process, in order to maintain catalyst activity and avoid side-reactions, both hydrogen and carbon monoxide must be present in the stream to be treated. This increases both the complexity of the system and its cost.

U.S. Pat. No. 4,664,753 discloses a method for iodine removal from acetic acid, acetic anhydride and/or ethylidene diacetate streams at a temperature of 20° to 250° C. The disclosed method requires a two component system consisting of (i) a phosphine or amine and (ii) zinc or compounds of zinc, copper, silver or cadmium. Treatment with this two-component system is followed by distillation. These chemical traps might be placed in a still bottom and continuously circulated through a reboiler. Contact (residence) times of 15 to 120 minutes are required and continuous replenishment is possible.

The process proposed in U.S. Pat. No. 4,664,753 utilizes a chemical trap comprising a two-component system which degrades with time. Furthermore, the materials formed by the reaction of the chemical traps with iodine or organic iodine-containing species may not be stable to the conditions of prolonged use. Furthermore, prolonged residence of active components of the chemical traps in the reboiler of the distillation train likely would result in fouling.

Finally, U.S. Pat. No. 4,029,553 describes a process for the purification of acetic acid containing very minor amounts of iodine by fractionation in a single column to obtain acetic acid containing 20 parts or less of iodine per billion parts acid as a liquid sidedraw from the column. In the operation of the process, very minor amounts of propionic acid and high-boiling impurities are withdrawn from the base of the column while removing a vapor from the top of the column and condensing and returning 90% or more of the overhead take-off to the upper section of the column. The iodine content of the crude acetic acid subjected to the purification process of U.S. Pat. No. 4,029,553 is in the parts per billion (ppb) range, e.g., 210 ppb I$^+$ and 30 ppb methyl iodide.

The present invention provides a process for the reduction in the iodine content of an acetyl product stream comprising (i) acetic acid or acetic anhydride and (ii) iodine, one or more iodine-containing compounds or a mixture thereof, which comprises the steps of:

(1) feeding the acetyl product stream to the middle or lower section of a distillation column containing a packing material comprising iron, nickel, copper or an alloy thereof; and (2) removing from the distillation column (i) a minor amount of acetic acid or anhydride vapor from the top of the column; (ii) a minor amount of acetic acid or anhydride liquid from the base of the column; and (iii) a major amount of purified acetic acid or anhydride from the upper section of the distillation column; wherein the purified acetic acid or anhydride contains less than about 200 ppb iodine and the amount of purified acetic acid or anhydride removed from the distillation column constitutes about 80 or more weight percent of the amount of the acetic acid product stream fed to the distillation column.

The process of this invention represents an improvement over the existing art as it (1) avoids the use of expensive noble-metal catalysts and (2) operates at moderate temperatures thus providing both an economic advantage as well as being compatible with the presence of acetic anhydride in the stream being treated. During the operation of the above-described process, the passage of the iodine-containing species through the above-described packing material is believed to result in an iodine/metal reaction, i.e., a reaction between the iodine-containing species and the iron, nickel and/or copper of the packing material.

The crude, iodine-containing, acetyl product stream normally is obtained from a carbonylation production system wherein methanol, dimethyl ether, methyl acetate and/or methyl iodide is contacted with carbon monoxide in the presence of a Group VIII-metal, elemental iodine and/or an iodine compound and, optionally, one or more promoters or primary catalyst stabilizers. The use of iodine in the carbonylation process leads to the formation of various iodine species, depending in part upon the various materials which may be included in the particular catalyst system or combination in use. Such iodine-containing impurities may comprise an alkyl iodide, e.g., methyl or ethyl iodide; an aryl iodide, e.g., iodobenzene; hydrogen iodide; iodine; a quaternary ammonium or phosphonium iodide; an iodide salt of a transition metal such as rhodium, iron, chromium, nickel, molybdenum, etc.; an iodide salt of an alkali or alkaline earth metal such as sodium, lithium, potassium, beryllium, magnesium, or calcium; an alkyl iodocarboxylic acid, e.g., methyl iodoacetate; or an iodoalkyl carboxylate, e.g., iodomethyl acetate. Unless stated otherwise, all references herein to "iodine" include all forms of iodine such as elemental iodine and the iodide compounds mentioned above.

The iodine content of the crude acetic acid product stream may be as high as 250 ppm but normally will be in the range of about 500 ppb to 10 ppm. Usually the iodine removal process of the invention will reduce the iodine content of the refined carboxyl product stream to less than about 200 ppb, preferably to less than 100 ppb, and most preferably to less than 20 ppb. The present process is particularly useful for reducing the iodine content of crude acetyl product streams which contain one or more aryl iodides, e.g., iodobenzene, resulting from the presence of an aryl or aromatic compound, such as a triarylphosphine, in the acetic acid or anhydride manufacturing process. The crude acetyl stream may contain from about 900 ppb to 4 ppm iodine in the form of one or more aryl iodides. However, the iodine removal process can be used to successfully remove iodine from acetyl streams resulting from various processes such as carbonylation processes using catalyst systems comprising rhodium, one or more iodine compounds and one or more promoters such as alkali metal salts and quaternary ammonium or phosphonium compounds. Generally, the degree of iodine removal depends, in part, on the concentration of iodine in the crude acetyl product stream. Thus, the degree of iodine removal which may be achieved by the use of the process of the present invention may be characterized by (1) the concentration of iodine in the acetyl product stream fed to the process relative to (2) the concentration of iodine in the refined acetic acid or anhydride produced by the process. The value of (1)/(2) may be in the range of about 150 to 500 but more typically will be in the range of about 200 to 300.

Other materials (in addition to those mentioned above) which may be present in very low concentrations in the crude acetyl product stream used as the feedstock in the process of this invention include methanol, methyl acetate, dimethyl ether, methyl iodide, water (when the acetyl stream does not contain acetic anhydride), and/or other materials endogenous to the catalytic carbonylation processes or decomposition products of such materials. Normally, the acetic acid or anhydride will constitute at least 95 weight percent, preferably at least 98 weight percent, of the crude acetyl product stream.

The temperature and pressure within the distillation column may vary considerably. Normal pressure of operation are from approximately atmospheric pressure (about 1 bar absolute) up to about 5 bar absolute although subatmospheric pressures may be employed if desired as well as superatmospheric pressures well in excess of 8 bar. The distillation column preferably is operated at a pressure within the range of about 1 to 3 bar absolute.

The temperature within the column normally will be between the boiling point of the acetic acid or anhydride being purified at the pressure of the column and the temperature at which a satisfactory boil-up rate is achieved at such pressure. At the preferred pressures, the column base temperature generally will be within the range of from approximately the boiling point of the acid or anhydride at the pressure employed to as high as about 205° C. Preferably, the column base temperature will not exceed 163° C. The preferred temperature ranges within the distillation column are about 110° to 130° C. for the purification of acetic acid and about 120° to 140° C. for the purification of acetic anhydride.

The essential components of the iodine-scavenging, packing material utilized in the purification process of the present invention comprises iron, nickel, copper or an alloy of one or more thereof. Iron typically is employed in the form of steel such as carbon steels, Bethanized steel, stainless steels, e.g., 300 and 400 series stainless steels and other iron-containing alloys. Carbon steels and 304 stainless steel generally are not preferred since they undergo relatively rapid corrosion and degradation, particularly in an acetic acid environment. Nickel may be used in the form of packing material constructed of substantially pure nickel or of nickel-containing alloys such as Hastelloy C nickel alloy. Similarly, copper may be used in substantially pure form or as a component of an alloy such as Monel copper-nickel alloy. It is apparent that the iodine-scavenging, packing materials may include, in addition to iron, nickel and/or copper, other metals such as chromium, molybdenum, cobalt, manganese, titanium, tungsten and/or vanadium commonly present in metal alloys. Such alloys also may contain minor amounts, e.g., up to about 10 weight percent of other elements or compounds such as alumina, silica, and the like. Normally, iron, nickel and/or copper will constitute at least 80 weight percent of the packing material.

The iodine-scavenging, packing material preferably is constructed of 316 stainless steel, nickel, copper or alloys of nickel and copper. Packing material constructed of copper-nickel alloys, e.g., Monel alloy, is a particularly preferred iodine-scavenging material. Such alloys are comprised of 50 to 80 weight percent nickel and 50 to 20 weight percent copper. The copper-nickel alloys may contain up to about 10 weight percent of one or more of the additional metals or compounds mentioned above.

The iodine-scavenging, packing material is utilized in the form of shaped articles, e.g., knitted wire mesh, rings, and saddles, commonly used as packing materials in commercial distillation operations. Generally, the surface area of the iodine-scavenging packing material is at least 1 meter square per liter.

The volume of the metal, iodine-scavenging, packing material required to purify a given amount of acetic acid or anhydride can vary significantly depending on a number of variables such as the iodine content of the acetyl product stream to be purified, the iodine concentration desired in the purified acetic acid or anhydride and the surface area of the iodine-scavenging material. To achieve a significant reduction in the iodine concentration of the crude acetyl stream fed to the distillation column, the liquid hourly space velocity (LHSV), i.e., the unit volume of acetyl feed per unit volume of iodine-scavenging packing material per hour, usually should not exceed 500. To achieve a reduction in iodine concentration by a factor of 50, e.g., from about 1 ppm to 20 ppb, the LHSV normally should be in the range of about 100 to 500, preferably in the range of about 200 to 300.

In the operation of the process of the present invention, the acetyl acid product stream to be purified is fed to the middle or lower section of a distillation column containing the metal, iodine-scavenging material. An acetic acid product stream may be obtained from a purification/dehydration process such as that described in U.S. Pat. No. 4,039,395.

Three streams are removed from the distillation column: (i) a minor amount of a vapor comprising acetic acid or anhydride and low boilers such as water, methyl iodide, methanol, methyl acetate, benzene, toluene and the like from the top of the column; (ii) a minor amount of a liquid comprising acetic acid or anhydride and iodine and/or iodine compounds from the base of the column; and (iii) a major amount of purified acetic acid or anhydride from the side of the upper section of the distillation column (sidedraw stream). Normally, the sidedraw stream of purified acetic acid or anhydride constitutes at least 80, preferably at least 90, weight percent of the acetyl product stream fed to the column. Thus, the total of the overhead vapor stream and the underflow liquid stream is less than 20, preferably less than 10, weight percent of the acetic acid fed to the column. Most of the iodine contained in the crude acetyl stream fed to the distillation column is removed, possibly as one or more metal iodide salts, in the liquid which is removed from the base of the column.

The iodine removal process of the present invention is further illustrated by the following examples. The iodine-containing acetic acid used in the examples was produced by the carbonylation of a mixture of methanol and methyl iodide in the presence of a catalyst system comprising a Group VIII metal and triphenyl phosphine. Thus, most portions of the acetic acid purified contained some iodobenzene.

The distillation column employed in the examples consisted of several different lengths of 1-inch diameter, silvered, vacuum-jacketed, glass columns. To a 1-liter, 3-neck flask equipped with an electric heating mantle was connected, in order, (1) a 36 inch section of the described 1-inch diameter, glass column, (2) a feed plate, (3) a 30 inch section of the described 1-inch diameter, glass column, (4) a feed plate, (5) a 6 inch section of the described 1-inch diameter, glass column, and (6) a vapor take-off head. The feed plate sections and the vapor take-off head were equipped with thermometers. Column section (1) contained 36 inches, column section (3) contains 30 inches, and column section 5 contains 6 inches, of Goodloe metal packing in the form of 1 inch diameter by 3 inches knitted wire mesh.

Crude acetic acid was fed to feed plate (2) and refined acetic acid is removed from the side of the column at feed plate (4). A small vapor stream was removed overhead through the vapor take-off head to remove trace amounts of low boiling impurities. A liquid stream was underflowed from the base to remove metal iodide salts and high boilers. The distillations involved in Examples 1–24 wherein iodine was removed from crude acetic acid were carried out at atmospheric pressures and at temperatures ranging from 120° C. in the base flask to a vapor take-off temperature of 116° C. The distillation of Example 25 wherein iodine was removed from crude acetic anhydride was carried out at atmospheric pressure and at temperatures ranging from about 140° C. in the base flask to a vapor take-off temperature of about 130° C.

The acetic acid removed from the top and bottom of the distillation column was analyzed for total iodine by X-ray analysis (sensitive to 5 ppm iodine). The purified sidedraw acetic acid is analyzed for iodine content by ion chromatography (sensitive to 10 ppb iodine). Since iodine present in the form of iodobenzene is not detected by ion chromatography analysis, some of the samples of the purified sidedraw acetic acid are pretreated to convert the iodobenzene to iodine compound(s) which are detected by ion chromatography. The analyses reported in Examples 19–21 did not include such a pretreatment and thus any iodobenzene present is not included in the iodine concentration reported in those examples. Metal analyses are done by ICP.

The crude acetic acid employed in the examples typically consists of 99+ weight percent acetic acid. Total iodine content of the crude acetic is determined by X-ray and/or ion chromatography analyses.

In Examples 1–18, the Goodloe metal packing employed was a knitted wire mesh of an alloy consisting of 33 weight percent copper and 67 weight percent nickel. This material is a commercial packing material available as MONEL Metal Goodloe packing.

EXAMPLE 1

A total of 7074 mL of acetic acid containing 4 ppm total iodine was fed at a rate of 200 mL per hour to the above described glass distillation column which contained 1.83 meters (72 inches) of the copper-nickel packing material. The total amount of vapor removed overhead constituted 4.0 weight percent of the crude acetic acid fed and contained less than 5 ppm iodine. The total amount of liquid removed from the base of the column constituted 0.9 weight percent of the crude acetic acid fed and contained 61 ppm iodine as metal iodide salts. The sidedraw stream of purified acetic acid contained less than 10 ppb iodine.

EXAMPLE 2

A total of 3142 mL of acetic acid containing 4 ppm total iodine was fed at a rate of 200 mL per hour to the distillation column as described in Example 1. The total amount of vapor removed overhead constituted 4.7 weight percent of the crude acetic acid feed and contained less than 5 ppm iodine. The total amount of liquid removed from the base of the column constituted 4.2 weight percent of the crude acetic acid feed and contained 77 ppm iodine as metal iodide salts. The sidedraw stream of purified acetic acid contained less than 10 ppb iodine.

EXAMPLE 3

A total of 3104 mL of acetic acid containing 3 ppm total iodine was fed at a rate of 200 mL per hour to the distillation column as described in Example 1. The total amount of vapor removed overhead constituted 5.2 weight percent of the crude acetic acid fed and contained less than 5 ppm iodine. The total amount of liquid removed from the base of the column constituted 3.8 weight percent of the crude acetic acid fed and contained 41 ppm iodine as metal iodide salts. The sidedraw stream of purified acetic acid contained less than 10 ppb iodine.

EXAMPLE 4

A total of 2950 mL of acetic acid containing 6 ppm total iodine was fed at a rate of 200 mL per hour to the distillation column as described in Example 1. The total amount of vapor removed overhead constituted 5.1 weight percent of the crude acetic acid fed and contained less than 5 ppm iodine. The total amount of liquid removed from the base of the column constituted 1.7 weight percent of the crude acetic acid fed and contained 67 ppm iodine as metal iodide salts. The sidedraw stream of purified acetic acid contained less than 10 ppb iodine.

EXAMPLE 5

A total of 3515 mL of acetic acid containing 5 ppm total iodine was fed at a rate of 200 mL per hour to the distillation column as described in Example 1. The total amount of vapor removed overhead constituted 2.8 weight percent of the crude acetic acid fed and contained less than 5 ppm iodine. The total amount of liquid removed from the base of the column constituted 4.7 weight percent of the crude acetic acid fed and contained 30 ppm iodine as metal iodide salts. The sidedraw stream of purified acetic acid contained less than 10 ppb iodine.

EXAMPLE 6

A total of 3570 mL of acetic acid containing 7 ppm total iodine was fed at a rate of 200 mL per hour to the distillation column as described in Example 1. The total amount of vapor removed overhead constituted 2.7 weight percent of the crude acetic acid fed and contained less than 5 ppm iodine. The total amount of liquid removed from the base of the column constituted 5.7 weight percent of the crude acetic acid fed and contained 51 ppm iodine as metal iodide salts. The sidedraw stream of purified acetic acid contained 13 ppb iodine.

EXAMPLE 7

A total of 1483 mL of acetic acid containing 5 ppm total iodine was fed at a rate of 200 mL per hour to the distillation column as described in Example 1. The total amount of vapor removed overhead constituted 3.5 weight percent of the crude acetic acid fed and contained less than 5 ppm iodine. The total amount of liquid removed from the base of the column constituted 3.5 weight percent of the crude acetic acid fed and contained 53 ppm iodine as metal iodide salts. The sidedraw stream of purified acetic acid contained less than 10 ppb iodine.

EXAMPLE 8

A total of 1533 mL of acetic acid containing 5 ppm total iodine was fed at a rate of 200 mL per hour to the glass distillation column described above except that the copper-nickel packing material between the feed plate and the sidedraw plate was reduced from 76.2 cm (30 inches) to 38.1 cm (15 inches). The total amount of vapor removed overhead constituted 3.9 weight percent of the crude acetic acid fed and contained less than 5 ppm iodine. The total amount of liquid removed from the base of the column constituted 6.2 weight percent of the crude acetic acid fed and contained 35 ppm iodine as metal iodide salts. The sidedraw stream of purified acetic acid contained 40 ppb iodine.

EXAMPLE 9

A total of 1666 mL of acetic acid containing 5 ppm total iodine was fed at a rate of 200 mL per hour to the distillation column according to the procedure and with the modification described Example 8. The total amount of vapor removed overhead constituted 2.7 weight percent of the crude acetic acid fed and contained less than 5 ppm iodine. The total amount of liquid removed from the base of the column constituted 5.7 weight percent of the crude acetic acid fed and contained 38 ppm iodine as metal iodide salts. The sidedraw stream of purified acetic acid contained 66 ppb iodine.

EXAMPLE 10

A total of 1648 mL of acetic acid containing 10 ppm total iodine was fed at a rate of 200 mL per hour to the glass distillation column described above except that the 38.1 cm (15 inches) of the copper-nickel packing material removed in Example 8 was replaced with 50.8 cm (20 inches) of Penn State packing material fabricated of Hastelloy C nickel-base alloy. The Penn State packing is in the form of metal ribbon 0.24 inches long having 100 tiny, protruded holes per square inch. The total amount of vapor removed overhead constituted 2.1 weight percent of the crude acetic acid fed and contained less than 5 ppm iodine. The total amount of liquid removed from the base of the column constituted 5.8 weight percent of the crude acetic acid fed and contained 58 ppm iodine as metal iodide salts. The sidedraw stream of purified acetic acid contained 38 ppb iodine.

EXAMPLE 11

A total of 1651 mL of acetic acid containing 3 ppm total iodine was fed at a rate of 200 mL per hour to the distillation column according to the procedure and with the modification described Example 10. The total amount of vapor removed overhead constituted 2.4 weight percent of the crude acetic acid fed and contained less than 5 ppm iodine. The total amount of liquid removed from the base of the column constituted 4.8 weight percent of the crude acetic acid fed and contained 57 ppm iodine as metal iodide salts. The sidedraw stream of purified acetic acid contained 20 ppb iodine.

EXAMPLE 12

A total of 1624 mL of acetic acid containing 3 ppm total iodine was fed at a rate of 200 mL per hour to the distillation column according to the procedure and with the modification described Example 10. The total amount of vapor removed overhead constituted 3.7 weight percent of the crude acetic acid fed and contained less than 5 ppm iodine. The total amount of liquid removed from the base of the column constituted 1.9 weight percent of the crude acetic acid fed and contained 72 ppm iodine as metal iodide salts. The sidedraw stream of purified acetic acid contained less than 10 ppb iodine.

EXAMPLE 13

A total of 1638 mL of acetic acid containing 6 ppm total iodine was fed at a rate of 200 mL per hour to the glass distillation column described above and employed in Example 1 except that the 0.91 meters (36 inches) of copper-nickel packing material below the feed plate was replaced with 0.91 meters of Penn State packing material fabricated of Hastelloy C alloy. The total amount of vapor removed overhead constituted 3.6 weight percent of the crude acetic acid fed and contained less than 5 ppm iodine. The total amount of liquid removed from the base of the column constituted 3.6 weight percent of the crude acetic acid fed and contained 8 ppm iodine as metal iodide salts. The sidedraw stream of purified acetic acid contained 18 ppb iodine.

EXAMPLE 14

A total of 1630 mL of acetic acid containing 10 ppm total iodine was fed at a rate of 200 mL per hour to the distillation column according to the procedure and with the modification described Example 13. The total amount of vapor removed overhead constituted 4.6 weight percent of the crude acetic acid fed and contained less than 5 ppm iodine. The total amount of liquid removed from the base of the column constituted 5.0 weight percent of the crude acetic acid fed and contained 11 ppm iodine as metal iodide salts. The sidedraw stream of purified acetic acid contained 50 ppb iodine.

EXAMPLE 15

A total of 1713 mL of acetic acid containing 3 ppm total iodine was fed at a rate of 200 mL per hour to the distillation column according to the procedure and with the modification described Example 13. The total amount of vapor removed overhead constituted 3.9 weight percent of the crude acetic acid fed and contained less than 5 ppm iodine. The total amount of liquid removed from the base of the column constituted 5.0 weight percent of the crude acetic acid fed and contained 39 ppm iodine as metal iodide salts. The sidedraw stream of purified acetic acid contained 26 ppb iodine.

EXAMPLE 16

A total of 1590 mL of acetic acid containing 3 ppm total iodine was fed at a rate of 200 mL per hour to the glass distillation column described above and employed in Example. 13 except that the 0.91 meters (36 inches) of Hastelloy C Penn State packing material was replaced with (1) 15.2 cm (6 inches) of the copper-nickel packing material employed in the preceding examples below the feed plate and (2) 76.2 cm (30 inches) of Goodloe packing material fabricated from Hastelloy C alloy below the 15.2 cm of the copper-nickel packing material. The total amount of vapor removed overhead constituted 4.1 weight percent of the crude acetic acid fed and contained less than 5 ppm iodine. The total amount of liquid removed from the base of the column constituted 5.0 weight percent of the crude acetic acid fed and contained 28 ppm iodine as metal iodide salts. The sidedraw stream of purified acetic acid contained 17 ppb iodine.

EXAMPLE 17

A total of 1648 mL of acetic acid containing 4 ppm total iodine was fed at a rate of 200 mL per hour to the distillation column according to the procedure and with the modification described Example 16. The total amount of vapor removed overhead constituted 3.1 weight percent of the crude acetic acid fed and contained less than 5 ppm iodine. The total amount of liquid removed from the base of the column constituted 5.0 weight percent of the crude acetic acid fed and contained 35 ppm iodine as metal iodide salts. The sidedraw stream of purified acetic acid contained less than 10 ppb iodine.

EXAMPLE 18

A total of 1613 mL of acetic acid containing 10 ppm total iodine was fed at a rate of 200 mL per hour to the distillation column according to the procedure and with the modification described Example 16. The total amount of vapor removed overhead constituted 3.7 weight percent of the crude acetic acid fed and contained less than 5 ppm iodine. The total amount of liquid removed from the base of the column constituted 5.0 weight percent of the crude acetic acid fed and contained 45 ppm iodine as metal iodide salts. The sidedraw stream of purified acetic acid contained 40 ppb iodine.

Based on 409 hours of operation of the glass distillation column containing 1.83 meters of the MONEL Metal Goodloe packing material, the rate of corrosion of this packing material was determined to be 102 microns per year.

EXAMPLE 19

In this experiment the metal packing material employed was Penn State Packing constructed of 304 stainless steel. A total of 3832 mL of acetic acid containing 17 ppm total iodine was fed at a rate of 250 mL per hour to the above described glass distillation column. The total amount of vapor removed overhead constituted 4.2 weight percent of the crude acetic acid fed and contained less than 5 ppm iodine. The total amount of liquid removed from the base of the column constituted 1.2 weight percent of the crude acetic acid fed and contained 43 ppm iodine as metal iodide salts. The sidedraw stream of purified acetic acid contained less than 10 ppb iodine. The rate of corrosion of the 304 stainless steel packing material was quite high.

EXAMPLE 20

In this experiment the Goodloe metal packing employed was a knitted wire mesh of 316 stainless steel. A total of 3635 mL of acetic acid containing 27 ppm total iodine was fed at a rate of 250 mL per hour to the above described glass distillation column. The total amount of vapor removed overhead constituted 4.3 weight percent of the crude acetic acid fed and contained 27 ppm iodine. The total amount of liquid removed from the base of the column constituted 0.6 weight percent of the crude acetic acid fed and contained 169 ppm iodine as metal iodide salts. The sidedraw stream of purified acetic acid contained 76–84 ppb iodine.

EXAMPLE 21

In this experiment, sections (1) and (3) of the 1-inch diameter, glass column contained 66 inches of 316 stainless steel Penn State packing and section (5) contained 6 inches of Goodloe copper packing as a knitted wire mesh. A total of 6000 mL of acetic acid containing 4 ppm total iodine was fed at a rate of 250 mL per hour to the above described glass distillation column. The total amount of vapor removed overhead constituted 5.1 weight percent of the crude acetic acid fed and contained 8 ppm iodine. The total amount of liquid removed from the base of the column constituted 3.1 weight percent of the crude acetic acid fed and contained 26 ppm iodine as metal iodide salts. The sidedraw stream of purified acetic acid contained less than 40 ppb iodine.

EXAMPLE 22

In this experiment the Goodloe metal packing employed was a knitted wire mesh of copper. A total of 3671 mL of acetic acid containing 4 ppm total iodine was fed at a rate of 200 mL per hour to the above described glass distillation column. The total amount of vapor removed overhead constituted 7.9 weight percent of the crude acetic acid fed and contained lees than 5 ppm iodine. The total amount of liquid removed from the base of the column constituted 3.8 weight percent of the crude acetic acid fed and contained 150 ppm iodine as metal iodide salts. The sidedraw stream of purified acetic acid contained 39 ppb iodine.

EXAMPLE 23

As in Example 22, the Goodloe metal packing employed in this experiment was a knitted wire mesh of copper. Furthermore, the distillation apparatus described hereinabove was modified by exchanging the 30-inch intermediate column section (3) for a section packed with 50 inches of Goodloe copper packing.

A total of 3549 mL of acetic acid containing 3 ppm total iodine was fed at a rate of 200 mL per hour to the above described glass distillation column. The total amount of vapor removed overhead constituted 8.4 weight percent of the crude acetic acid fed and contained less than 5 ppm iodine. The total amount of liquid removed from the base of the column constituted 3.4 weight percent of the crude acetic acid fed and contained 146 ppm iodine as metal iodide salts. The sidedraw stream of purified acetic acid contained less than 10 ppb iodine.

EXAMPLE 24

In this experiment, the lower 20 inches of 36 inch section (1) of the distillation column were filled with Goodloe Hastelloy C packing and the upper 16 inches were filled with Goodloe nickel packing. Intermediate section (3) contained 30 inches of Goodloe nickel packing and upper section 5 was packed with 6 inches of Goodloe Hastelloy C packing.

A total of 1694 mL of acetic acid containing 3 ppm total iodine was fed at a rate of 200 mL per hour to the above described glass distillation column. The total amount of vapor removed overhead constituted 3.5 weight percent of the crude acetic acid fed and contained lees than 5 ppm iodine. The total amount of liquid removed from the base of the column constituted 3.1 weight percent of the crude acetic acid fed and contained 57 ppm iodine as metal iodide salts. The sidedraw stream of purified acetic acid contained 10 ppb iodine.

EXAMPLE 25

The modified apparatus described in Example 16 was used to remove iodine from acetic anhydride. A total of 4000 mL of acetic anhydride containing 1.3 ppm total iodine was fed at a rate of 250 mL per hour to the distillation column. The total amount of vapor removed overhead constituted 1.8 weight percent of the crude acetic anhydride fed and contained less than 5 ppm iodine. The total amount of liquid removed from the base of the column constituted 0.7 weight percent of the crude acetic anhydride fed and contained less than 5 ppm iodine as metal iodide salts. The sidedraw stream of purified acetic anhydride contained 23 ppb iodine.

The invention has been described in detail with particular reference to preferred embodiments thereof, but it will be understood that variations and modifications may be effected within the spirit and scope of the invention.

We claim:

1. Process for the reduction in the iodine content of an acetyl product stream comprising (i) acetic acid or acetic anhydride and (ii) about 500 parts per billion to 10 parts per million iodine in the form of iodine, one or more iodine-containing compounds or a mixture thereof, which comprises the steps of:

(1) feeding the acetyl product stream to the middle or lower section of a distillation column containing a packing material constructed of iron, nickel, copper, or an alloy thereof; and (2) removing from the distillation column (i) a minor amount of acetic acid or anhydride vapor from the top of the column; (ii) a minor amount of acetic acid or anhydride liquid from the base of the column; and (iii) a major amount of purified acetic acid or anhydride from the upper section of the distillation column; wherein (a) the purified acetic acid or anhydride contains less than about 200 ppb iodine; (b) the amount of purified acetic acid or anhydride removed from the distillation column constitutes about 80 or more weight percent of the amount of the acetyl product stream fed to the distillation column; (c) most of the iodine contained in the acetyl product stream fed to the distillation column is removed in the liquid which is removed from the base of the column; and (d) the liquid hourly space velocity of the acetyl product stream fed to the distillation column is about 100 to 500, in which liquid hourly space velocity is the unit volume of acetyl product stream feed per unit volume of packing material defined in step (1).

2. Process according to claim 1 wherein the packing material is constructed of 316 stainless steel, nickel, copper, or an alloy of nickel and copper;

the purified acetic acid or anhydride contains less than about 100 ppb iodine; and the amount of purified acetic acid or anhydride removed from the distillation column constitutes about 90 or more weight percent of the amount of the acetyl product stream fed to the distillation column.

3. Process for the reduction in the iodine content of an acetyl product stream comprising (i) acetic acid and (ii) about 500 parts per billion to 10 parts per million iodine in the form of iodine, one or more iodine-containing compounds or a mixture thereof, which comprises the steps of:

(1) feeding the acetyl product stream to the middle or lower section of a distillation column containing a packing material constructed of iron, nickel, copper, or an alloy thereof and maintained at a temperature of about 110° to 130° C.; and (2) removing from the distillation column (i) a minor amount of acetic acid vapor from the top of the column; (ii) a minor amount of acetic acid liquid from the base of the column; and (iii) a major amount of purified acetic acid from the upper section of the distillation column; wherein (a) the purified acetic acid contains less than about 200 ppb iodine; the amount of purified acetic acid removed from the distillation column constitutes about 80 or more weight percent of the amount of the acetyl product stream fed to the distillation column; (c) most of the iodine contained in the acetyl product stream fed to the distillation column is removed in the liquid which is removed from the base of the column; and (d) the liquid hourly space velocity of the acetyl product stream fed to the distillation column is about 100 to 500, in which liquid hourly space velocity is the unit volume of acetyl product stream feed per unit volume of packing material defined in step (1).

4. Process according to claim 3 wherein the purified acetic acid contains less than about 100 ppb iodine; the liquid hourly space velocity of the acetyl product stream fed to the distillation column is about 100 to 500; the packing material is in the form of knitted wire mesh; and the amount of purified acetic acid removed from the distillation column constitutes about 90 or more weight percent of the amount of the acetyl product stream fed to the distillation column.

5. Process for the reduction in the iodine content of an acetyl product stream comprising (i) acetic acid and (ii) about 500 parts per billion to 10 parts per million iodine in the form of iodine, one or more iodine-containing compounds or a mixture thereof, which comprises the steps of:

(1) feeding the acetyl product stream to the middle or lower section of a distillation column containing a packing material constructed of a nickel-copper alloy comprising 50 to 80 weight percent nickel and 50 to 20 weight percent copper and maintained at a temperature of about 110° to 130° C.; and (2) removing from the distillation column (i) a minor amount of acetic acid vapor from the top of the column; (ii) a minor amount of acetic acid liquid from the base of the column; and (iii) a major amount of purified acetic acid from the upper section of the distillation column; wherein (a) the purified acetic acid contains less than about 100 ppb iodine; (b) the amount of purified acetic acid removed from the distillation column constitutes about 80 or more weight percent of the amount of the acetyl product stream fed to the distillation column; (c) most of the iodine contained in the acetyl product stream fed to the distillation column is removed in the liquid which is removed from the base of the column; and (d) the liquid hourly space velocity of the acetyl product stream fed to the distillation column is about 200 to 300, in which liquid hourly space velocity is the unit volume of acetyl product stream feed per unit volume of packing material defined in step (1).

6. Process according to claim 5 wherein the packing material is in the form of knitted wire mesh; the purified acetic acid contains less than about 20 ppb iodine; and the amount of purified acetic acid or anhydride removed from the distillation column constitutes about 90 or more weight percent of the amount of the acetyl product stream fed to the distillation column.

7. Process according to claim 4 wherein the iodine-containing compounds comprise one or more aryl iodides.

8. Process according to claim 5 wherein the iodine-containing compounds comprise 900 parts per billion to 4 parts per million of one or more aryl iodides; the packing material is in the form of knitted wire mesh; the purified acetic acid contains less than about 20 ppb iodine; and the amount of purified acetic acid or anhydride removed from the distillation column constitutes about 90 or more weight percent of the amount of the acetyl product stream fed to the distillation column.

* * * * *